United States Patent [19]
Felch et al.

[11] Patent Number: 4,807,994
[45] Date of Patent: Feb. 28, 1989

[54] METHOD OF MAPPING ION IMPLANT DOSE UNIFORMITY

[75] Inventors: Susan B. Felch, Los Altos; Ronald A. Powell, Redwood City, both of Calif.

[73] Assignee: Varian Associates, Inc., Palo Alto, Calif.

[21] Appl. No.: 123,073

[22] Filed: Nov. 19, 1987

[51] Int. Cl.$^4$ ............................................. G01J 3/42
[52] U.S. Cl. .................................... 356/326; 356/328
[58] Field of Search ............................... 356/326, 328

[56] References Cited

U.S. PATENT DOCUMENTS 4,676,647  6/1987  Kikkawa et al. ................... 356/328

OTHER PUBLICATIONS

Badalic and Runge, "A New Method to Monitor the Beam Profile in High-Current Ion Implantation Systems," J. Phys. E: Sci. Instrum., vol. 12, 1979.
Badalec and Runge, "Thin Silicon Films for Ion Beam Monitoring," Inst. Phys. Conf. Ser. No. 54, Chapter 3, 1980, pp. 91-94.
Ch. Kuhl, et al., "Optical Investigation of Different Silicon Films," Muchen, Germany.
Aspnes and Studna, "Dielectric Functions and Optical Parameters of Si, Ge, GaP, GaAs, GaSb, InP, InAs, and InSb from 1.5 to 6.0 eV," Physical Review B, vol. 27, No. 2, Jan. 15, 1983.
Richard Carl Eden, "Photoemission Studies of the Electronic Band Structures of Gallium Arsenide, Gallium Phosphide, and Silicon," May 1967, pp. 286 and 297.
Golin, Schell and Glaze, "Advanced Methods of Ion Implant Monitoring Using Optical Dosimetry," Solid State Technology, Jun. 1985, pp. 155-163.

Primary Examiner—Vincent P. McGraw
Attorney, Agent, or Firm—Stanley Z. Cole; Kenneth L. Warsh; Gerald M. Fisher

[57] ABSTRACT

A method of mapping implanted ion dose uniformity is disclosed in which wafers of polysilicon-on-silicon or polysilicon-on-oxidized-silicon are implanted with the ion dose to be mapped and then scanned in a spectrophotmeter using monochromatic radiation. An interference spectral technique is used to achieve improved sensitivity while preserving thermal and electrical properties close to those of actual devices.

6 Claims, 8 Drawing Sheets

DOSE 1 < DOSE 2

FIG.14

METHOD OF MAPPING ION IMPLANT DOSE UNIFORMITY

FIELD OF THE INVENTION

This invention pertains to a method of mapping the uniformity of the dose of charged ions implanted in semiconductor wafers.

BACKGROUND OF THE INVENTION

Because doping of materials by ion beam implantation is unique in utilizing fine scale electrostatic processes, as distinct from large scale diffusion or thermochemical processes, the problem of monitoring implantation uniformities is complex and demanding. The importance of the spatial structure of the dose, as affected by the spatial position and lateral profile of the beam, for accurate yield verification and characterization is unquestionable. VLSI process engineers concerned with yield must certainly concern themselves with fine scale dose nonuniformities, because of the fine dimensions and narrow dose tolerances of the devices being fabricated. Crystal beam scanners of varying sophistication offer hope for some of the most severe problems encountered, but they cannot be designed to insure against their own failures and must be periodically monitored in the production environment.

Other crude monitoring systems of the prior art include Faraday cups and some radiation-sensitive foil such as Mylar. Both methods have serious drawbacks. Faraday cups have a very limited spatial resolution, and it is usually impossible to obtain reliable information on the lateral extension of the ion beam. Radiation sensitive hydrocarbon foils lead to outgassing and contamination of the target chamber. They cannot be used in high current systems as thermal decomposition will destroy the foils.

At the lower limits of dose and energy, typical beam diameters shrink to a few millimeters or less, aggravating the already difficult problems of design of uniform scan systems. Therefore, high resolution measurement techniques free from other process steps must be used. Optical dosimetry has the unique capability of resolving these structural dose non-uniformity patterns in a simple-to-use real-time measurement.

The best prior art techniques used the darkening (i.e., reduced transmission to visible light) of an epitaxial silicon-on-sapphire film after ion implantation to measure implanted dose. Using this technique, the minimum doses one could measure were quite high, $>5 \times 10^{12}$ cm$^{-2}$.

OBJECTS OF THE INVENTION

An object of the invention is to provide a method of mapping ion implant dose uniformity in semiconductor wafers.

A further object of the invention is to make such a method usable in wafer processing machines for large-diameter wafers.

Another object of the invention is to limit the method to commonly available low-cost materials.

Still another object of the invention is to preserve the basic electrical and thermal properties of actual silicon device wafers in the method.

SUMMARY OF THE INVENTION

These objects of the invention and other objects, features and advantages to become apparent as the specification progresses are accompanied by the invention according to which, briefly stated, a method for measurement is disclosed in which implantation causes a wavelength shift in the interference spectrum of transmitted or reflected radiation from thin film/substrate combinations (e.g., epitaxial silicon-on-sapphire and polysilicon-on-quartz.) By sensing the optimum wavelength, one can detect changes in transmitted (or reflected) light which correlate with implant dose. For some wavelengths, increased dose could actually increase the measured transmission due to thin film-substrate optical interference effects. Unlike earlier work, this approach is especially well suited to the low-dose range ($<10^{14}$ cm$^{-2}$). Furthermore, the method of this invention uses inexpensive polysilicon films and quartz substrates which are available in large-diameter (8-inch) wafers, unlike sapphire. Also, the method of this invention is applicable to polysilicon-on-oxidized-Si substrates. The latter choice of materials avoids the use of quartz substrates and preserves the basic thermal and electrical properties of actual silicon device wafers.

These and further constructional and operational characteristics of the invention will be more evident from the detailed description given hereinafter with reference to the figures of the accompanying drawings alternatives by way of non-limiting examples.

GLOSSARY

The following is a glossary of terms, elements, and structural members as referenced and employed in the present invention.

| 10    | wafer                         |
|-------|-------------------------------|
| 12    | monochromator                 |
| 14    | primary detector              |
| 16,18 | lenses                        |
| 20,22 | irises                        |
| 24    | IR filter                     |
| 26    | partially-transmitting mirror |
| 28    | light chopper                 |
| 30    | driver                        |
| 32    | tungsten lamp                 |
| 34    | stabilized power supply       |
| 36    | reference detector            |
| 38    | lens                          |
| 40,42 | preamplifiers                 |
| 44    | lock-in amplifier             |
| 46    | computer                      |
| 48    | monitor                       |
| 50    | disc-drive                    |
| 52    | printer                       |
| 54    | motorized translation stage   |

DETAILED DESCRIPTION OF THE PREFERRED EMBODIMENTS

Measuring the transmission of the broad-band, visible light through an ion-implanted silicon-on-sapphire (SOS) wafer has been proposed in the prior art as an implant dosimetry technique, since it has been found that the implanted ions damage the crystal structure of the epitaxial silicon film and change its optical absorption coefficient, making it darken with increasing dose. (See: Golin et al, *Solid State Technology* 28, 155, June 1985; Badalec et al, *Institute of Physics Conference Series*, No. 54, Chap. 3, pp. 91–94). However, the exact relationship between implanted dose and transmission spectrum was virtually unexplored. This is particularly true at low doses ($<10^{12}$ cm$^{-2}$), where more sensitive dosimetry techniques needed to be developed. By carrying out a detailed theoretical and experimental analysis of the transmission spectrum of implanted thin film/substrate combinations and taking advantage of optical interference effects, a far more sensitive technique for dose mapping has been developed.

Figure 1:
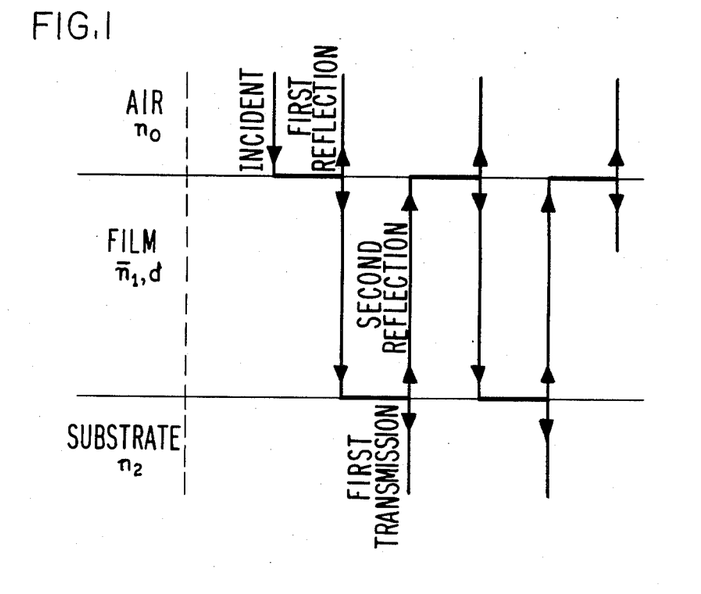
FIG. 1 is a schematic diagram showing the amplitudes of light for an absorbing thin film in the case of multiple interference at normal incidence.

The transmission coefficient at wavelength $\lambda$ of a thin silicon film on a transparent substrate in air can be calculated using standard optical theory. (See: Kuhl et al, *J. Electrochem. Soc.*, 121, 1496, 1974.) Multiple reflections take place at the front and back surfaces of the film, and the amplitude of the light at each reflection or transmission is shown in FIG. 1. The film has thickness d and index of refraction $n_{Si}$. The substrate is semi-infinite and has index of refraction $n_{sub}$. If we apply the method of summation, we find that the complex transmitted amplitude for normal incidence is given by:

$$t = t_1 t_2 \exp[-(\alpha d/2) - i\delta] - t_1 t_2 r_1 r_2 \exp[-(3\alpha d/2) - 3i\delta] + \quad (1)$$
$$t_1 t_2 r_1^2 r_2^2 \exp[-(5\alpha d/2) - 5i\delta] + \ldots$$
$$= t_1 t_2 \exp[-(\alpha d/2) - i\delta]/\{1 - r_1 r_2 \exp[-\alpha d - 2i\delta]\}$$

where $\alpha$ is the absorption coefficient of the silicon ($\alpha = 4\zeta\kappa/\lambda$) and $\delta = 2\zeta n_{Si} d/\lambda$ is the phase change that occurs on one traversal of the silicon layer. Here, $r_1$ and $r_2$ ($t_1$ and $t_2$) are the amplitude reflectivities (transmissivities) of the silicon-air and silicon-substrate interfaces, respectively. These amplitudes are determined by the indices of refraction of silicon, substrate, and air (n=1). Namely, $$r_1 = [n_{Si} - 1]/[n_{Si} + 1]; \quad (2)$$
$$r_2 = [n_{Si} - n_{sub}]/[n_{Si} + n_{sub}];$$
$$t_1 = 2/[n_{Si} + 1];$$
$$t_2 = 2n_{Si}/[n_{Si} + n_{sub}]$$

If we assume that $\kappa << n$ (which is valid for silicon at wavelengths greater than 400 nm), then $r_1$, $r_2$, $t_1$, and $t_2$ are real. With that approximation, the transmission coefficient is $$T = tt^* = \frac{t_1^2 t_2^2 \exp[-\alpha d]}{1 - \{2r_1 r_2 \exp[-\alpha d]\cos[2\delta]\} + r_1^2 r_2^2 \exp[-2\alpha d]} \quad (3)$$

We have also assumed that the transmission of the substrate (sapphire or quartz) is a constant independent of wavelength. This is very nearly true for $\lambda > 400$ nm and can be taken into account by multiplying the expression in Eqn. 3 by an appropriate constant less than unity.

Eqn. 3 predicts that the transmission will oscillate as the wavelength is varied. Maxima will occur when $\delta = j\pi$ where j is an integer; that is, at wavelengths $$\lambda_j = 2dn/j, \text{ where } j = 1, 2, 3 \ldots \quad (4).$$

Similarly, minima will occur at wavelengths $\lambda_k = 2dn/k$, where $k = j - \frac{1}{2}$, or $$\lambda_k = 2dn/(j - \frac{1}{2}), \text{ where } j = 1, 2, 3, \ldots \quad (5).$$

Figure 2:
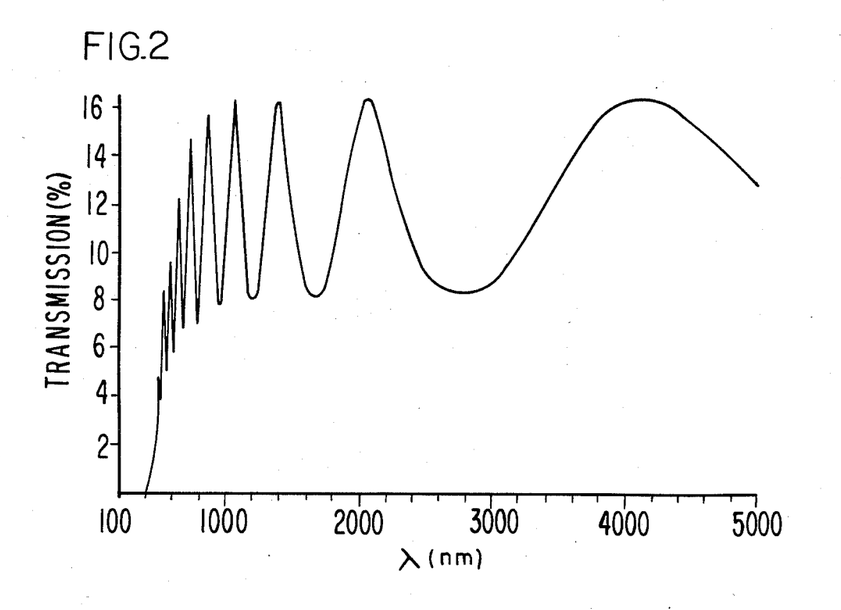
FIG. 2 is a plot of Eqn. 3 for wavelengths between 200 nm and 5000 nm.
Figure 3:
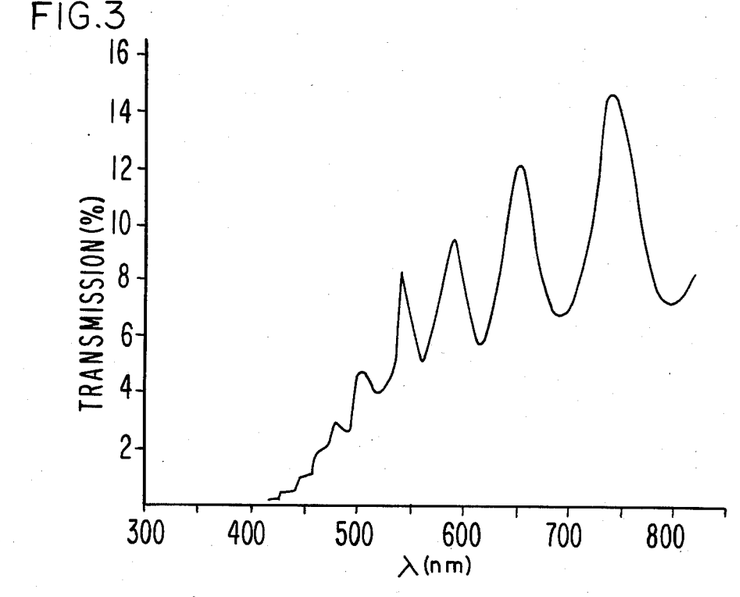
FIG. 3 is an expanded view of the plot shown in FIG. 2 for the wavelengths 300 nm to 800 nm.

A plot of Eqn. 3 for wavelengths between 200 nm and 5000 nm is presented in FIG. 2. A film thickness of 600 nm was used for calculation, and values for $n(\lambda)$ and $\alpha(\lambda)$ for crystalline silicon were taken from Aspnes et al and Eden. (See: Aspnes et al, *Phys. Rev.*, B27, 985 (1983); R.C. Eden, Ph.D. Thesis, Department of Electrical Engineering, Stanford University, 1967.) In addition, the entire curve has been multiplied by a scale factor so that it can be more easily compared with experimental silicon-on-sapphire transmission spectra to be presented later. The oscillations are very clear and sharp and become denser (more closely spaced) for shorter wavelengths. An expanded view of the theoretical spectrum from 300 nm to 800 nm is given in FIG. 3. This region of wavelengths is the one that is available with common UV/visible spectrophotometers and thus could easily be studied. Two interesting features of this short-wavelength curve are that at least six oscillations can easily be discerned, and that the amplitudes of the two envelopes of the curve increase as wavelength increases.

When ions are implanted into silicon, they damage the crystalline lattice structure. This damage, in turn, changes the index of refraction, n, and the absorption coefficient $\alpha$ (or extinction coefficient $\kappa = \alpha\lambda/[4\pi]$) of the silicon. For a silicon-on-sapphire or a polysilicon-on-quartz wafer, this will show up as a change in the transmission spectrum. The wavelengths of maximum and minimum transmission, $\lambda_j$ and $\lambda_k$, will be altered. In addition, the amplitudes of the two envelopes of the curve will change. Since the lattice damage increases as the implanted ion dose is increased for a given ion energy and ion species, the shifts in $\lambda_j$ and $\lambda_k$ and the changes in the transmission envelopes will be monotonic functions of the implant dose. These facts form the basis of these transmission studies.

The following transmission spectra were taken using a Beckman spectrophotometer. The instrument has both visible and ultraviolet sources and detectors, so it can measure transmission at wavelengths ranging from 190 to 800 nm. The reference spectrum to which the spectra of all measured samples are compared is that of air (no wafer in the spectrometer).

Figure 4:
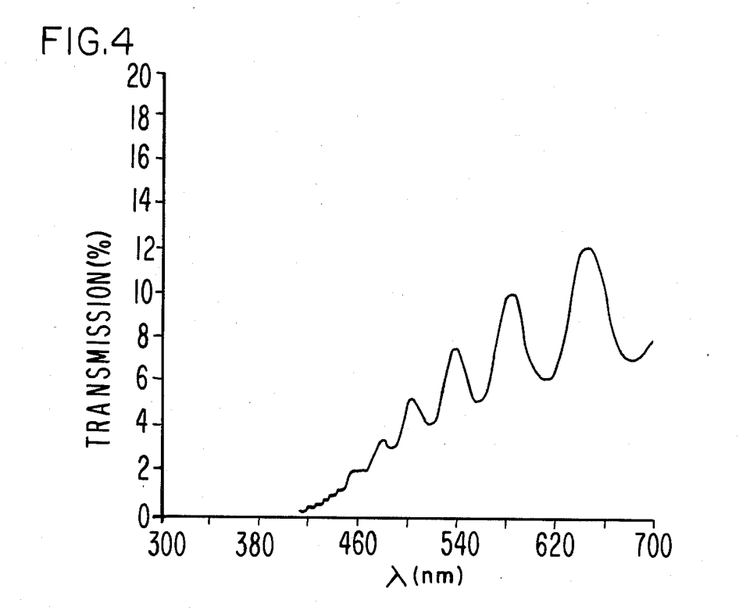
FIG. 4 is a measured transmission spectrum of an unimplanted silicon-on-sapphire (SOS) wafer.

FIG. 4 is a transmission spectrum of an unimplanted silicon-on-sapphire wafer. The epitaxial silicon layer (measured by a Dektak profilometer) is 600 nm thick. This spectrum is seen to be nearly identical to the theoretical one plotted in FIG. 3. For both, the transmission is zero for wavelengths below 400 nm, where the absorption coefficient of crystalline silicon is very large ($>10^5$ cm$^{-1}$). As Table I indicates, the observed maxima and minima of the oscillations occur at theoretically predicted wavelengths. These similarities give us confidence in the theoretical model for the transmission spectrum (Eqn. 3).

TABLE I

Theoretical and experimental values of $\lambda_j$ for an unimplanted silicon-on-sapphire wafer.

| j | Theoretical $\lambda_j$ (nm) | Experimental $\lambda_j$ (nm) |
|---|---|---|
| 7 | 660 | 644 |
| 8 | 592 | 584 |
| 9 | 549 | 538 |
| 10 | 516 | 502 |
| 11 | 480 | 478 |
| 6.5 | 698 | 682 |
| 7.5 | 624 | 611 |
| 8.5 | 568 | 566 |
| 9.5 | 533 | 518 |
| 10.5 | 499 | 484 |

Figure 5:
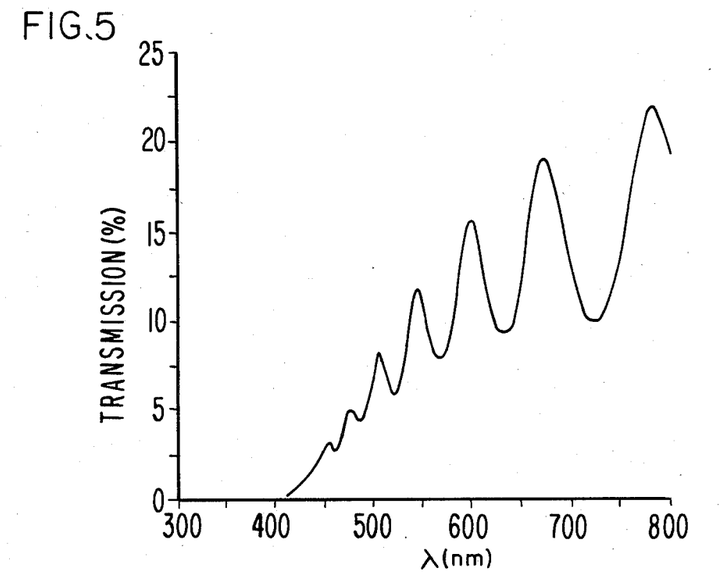
FIG. 5 is a measured transmission spectrum of an SOS wafer implanted with 100-keV As$^+$ at $5 \times 10^{10}$ cm$^{-2}$.
Figure 6:
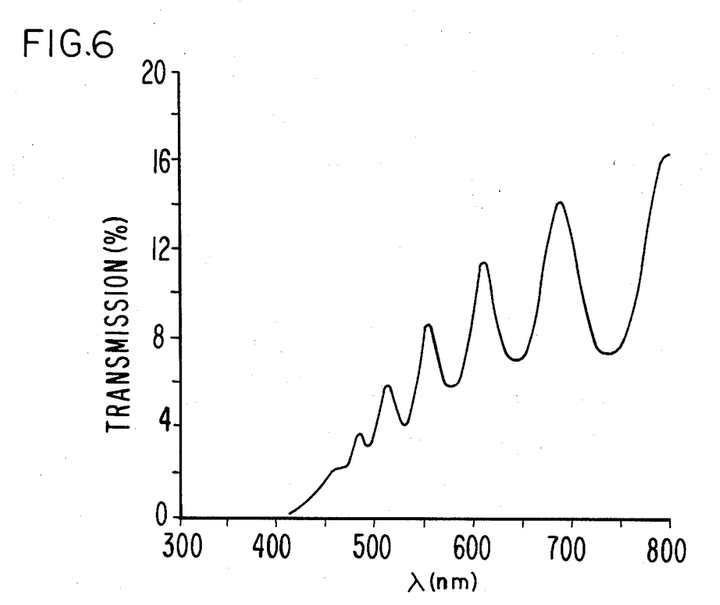
FIG. 6 is a measured transmission spectrum of an SOS wafer implanted with 100-keV As$^+$ at $5 \times 10^{11}$ cm$^{-2}$.
Figure 7:
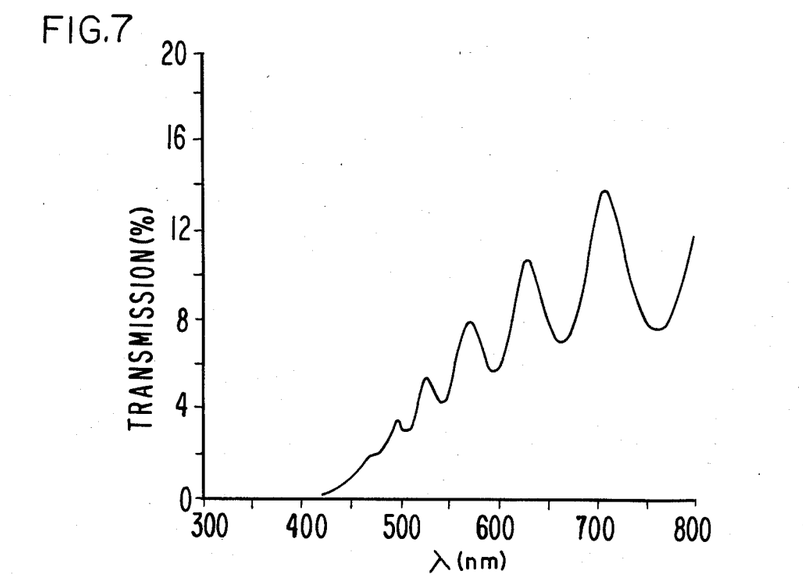
FIG. 7 is a measured transmission spectrum of an SOS wafer implanted with 100-keV As$^+$ at $1 \times 10^{13}$ cm$^{-2}$.

The transmission spectra for wavelengths between 300 nm and 800 nm of three implanted silicon-on-sapphire wafers are presented in FIGS. 5-7. All of the wafers were implanted with 100-keV As+ ions. Both the implant dopant profile and damage are confined to a region at the surface of <100 nm, which is much less than the 600 nm film thickness. The dose for the wafer of FIG. 5 was $5.0 \times 10^{10}$ cm$^{-2}$, the dose for that of FIG. 6 was $5.0 \times 10^{11}$ cm$^{-2}$, and the dose for that of FIG. 7 was $1.0 \times 10^{13}$ cm$^{-2}$. One can see that as the dose increases, the wavelength $\lambda_j$ at which the j-th maximum or minimum occurs shifts to longer wavelengths. In addition, the two envelopes of the spectrum move to lower transmission values as the dose increases. The wavelengths at which the j=7 and j=8 maxima occur as a function of dose are listed in Table II. The $5 \times 10^{10}$ cm$^{-2}$ and $1 \times 10^{11}$ cm$^{-2}$ dose implants are seen to produce nearly identical transmission spectra in the range shown (300-800 nm). This is not surprising, since the uncertainty in the determination of $\lambda_j$ using the Beckman spectrophotometer was 2 nm. However, doses above $5 \times 10^{11}$ cm$^{-2}$ can be determined to better than 10%. In order to have a similar sensitivity for doses as low as $5 \times 10^{10}$ cm$^{-2}$, one needs to look at the shift of a maximum that occurs in the infrared with an instrument that still has a resolution of 2 nm. The j=3 maxima for doses of $5 \times 10^{10}$ cm$^{-2}$ and $1 \times 10^{11}$ cm$^{-2}$ should be separated by about 10 nm so that changes in dose of $1 \times 10^{10}$ cm$^{-2}$ would be discernible in that low-dose range.

TABLE II $\lambda_j$ versus dose for silicon-on-sapphire wafers.

| Dose (cm$^{-2}$) | $\lambda_7$ (nm) | $\lambda_8$ (nm) |
|---|---|---|
| 0 | 645 | 583 |
| $5 \times 10^{10}$ | 673 | 599 |
| $1 \times 10^{11}$ | 677 | 600 |
| $5 \times 10^{11}$ | 689 | 610 |
| $1 \times 10^{12}$ | 712 | 630 |
| $5 \times 10^{12}$ | 753 | 665 |
| $1 \times 10^{13}$ | >800 | 710 |

Figure 8:
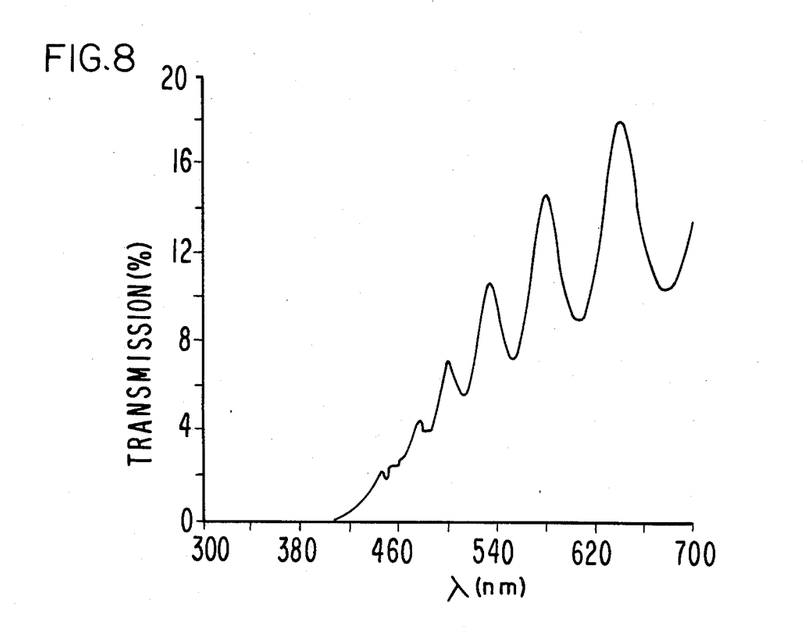
FIG. 8 is a measured transmission spectrum of an SOS wafer that has been implanted with 100-keV As$^+$ at $1 \times 10^{15}$ cm$^{-2}$ and rapidly annealed at 1050° C. for 30 seconds.

A nice feature of this dosimetry technique is that annealing an implanted silicon-on-sapphire wafer removes the damage to the epitaxial silicon and returns its transmission spectrum to that of an unimplanted wafer. The spectrum of a wafer that had been heavily implanted with a dose of As+ at $1 \times 10^{15}$ cm$^{-2}$ and then rapidly annealed in a rapid thermal processor at a temperature of 1050° C. for 30 seconds is presented in FIG. 8. This curve is identical to the one of FIG. 4, taken with an unimplanted silicon-on-sapphire wafer. This means that the relatively expensive silicon-on-sapphire wafers can be recycled by annealing them after each implant and transmission measurement, making the overall cost of the dose-monitoring technique more reasonable. On the other hand, it is difficult to obtain large silicon-on-sapphire wafers (6-8 inch diameter) needed to characterize the next generation implanters. Also, the effect on the transmission curve of the increasing concentration of electrically activated dopants in the recycled silicon-on-sapphire wafer needs to be determined.

Polysilicon-on-quartz wafers as an alternative to silicon-on-sapphire wafers have also been examined. Quartz ($SiO_2$) wafers are much cheaper than sapphire ($Al_2O_3$) ones and can be readily obtained in large diameters comparable to commercial silicon substrates (4-8 inches). In addition, LPCVD deposition of a polysilicon film is considerably easier than growth of an epitaxial silicon layer. However, while it may be possible to recycle polysilicon-on-quartz wafers by annealing them, the polysilicon grain size and size distribution may be altered. In this case, one would need to etch the polysilicon away and deposit a new film.

Figure 9:
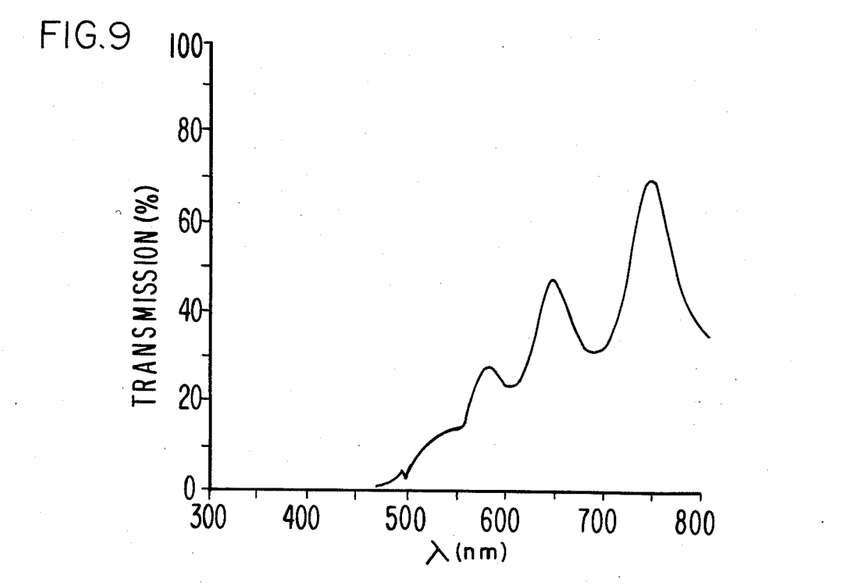
FIG. 9 is a measured transmission spectrum of an unimplanted polysilicon-on-quartz (POQ) wafer.

The transmission spectrum of an unimplanted polysilicon-on-quartz wafer is shown in FIG. 9. The polysilicon film is 550 nm thick. As for the silicon-on-sapphire wafers, the transmission is seen to oscillate as a function of wavelength; however, the polysilicon-on-quartz oscillations are spread out more. Also, the absolute transmission values for the polysilicon-on-quartz wafers are much larger than those for the silicon-on-sapphire wafers. This is because the quartz wafer was polished on both sides while the sapphire wafer used in these studies was frosted on one side, scattering much of the transmitted light away from the detector. Theoretical estimates of the wavelengths at which oscillation maxima occur can be made by using the graph of refractive index versus wavelength for polysilicon found in Kuhl et al. These theoretical predictions are compared in Table III with the experimental results for three maxima. Again, the good agreement demonstrates that we understand the phenomenon being observed.

TABLE III

Theoretical and experimental values of $\lambda_j$ for an unimplanted polysilicon-on-quartz wafer.

| j | Theoretical $\lambda_j$ (nm) | Experimental $\lambda_j$ (nm) |
|---|---|---|
| 6 | 750 | 749 |
| 7 | 644 | 649 |
| 8 | 564 | 582 |

Figure 10:
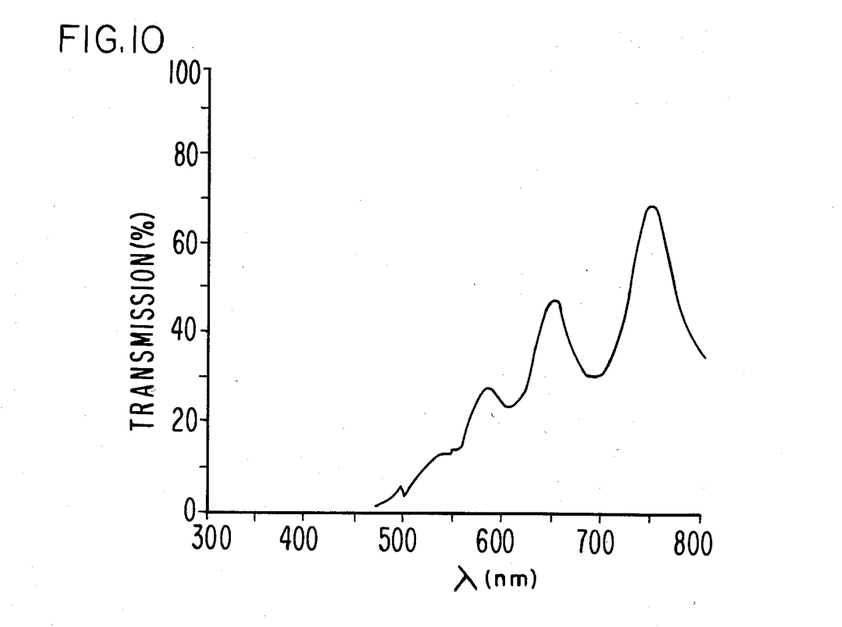
FIG. 10 is the measured transmission spectrum of a POQ water implanted with 100-keV As$^+$ at $5 \times 10^{10}$ cm$^{-2}$.
Figure 11:
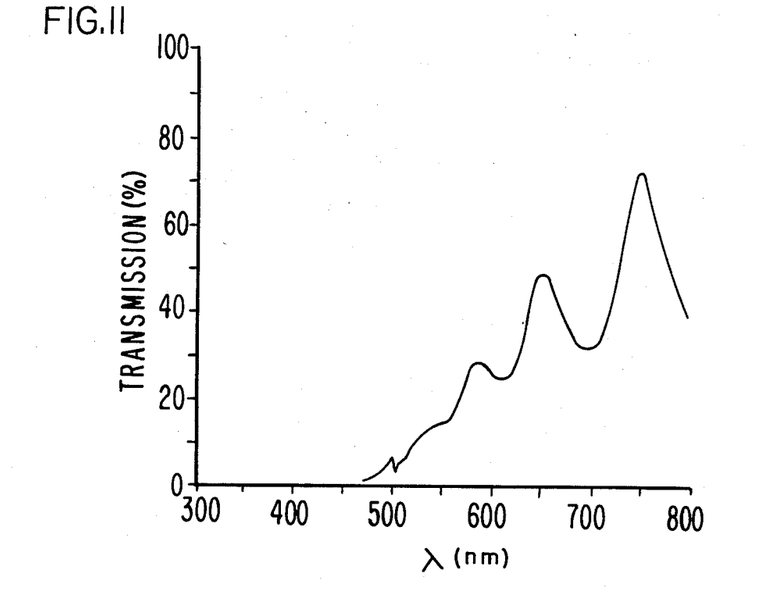
FIG. 11 is the measured transmission spectrum of a POQ water implanted with 100-keV As$^+$ at $1 \times 10^{11}$ cm$^{-2}$.
Figure 12:
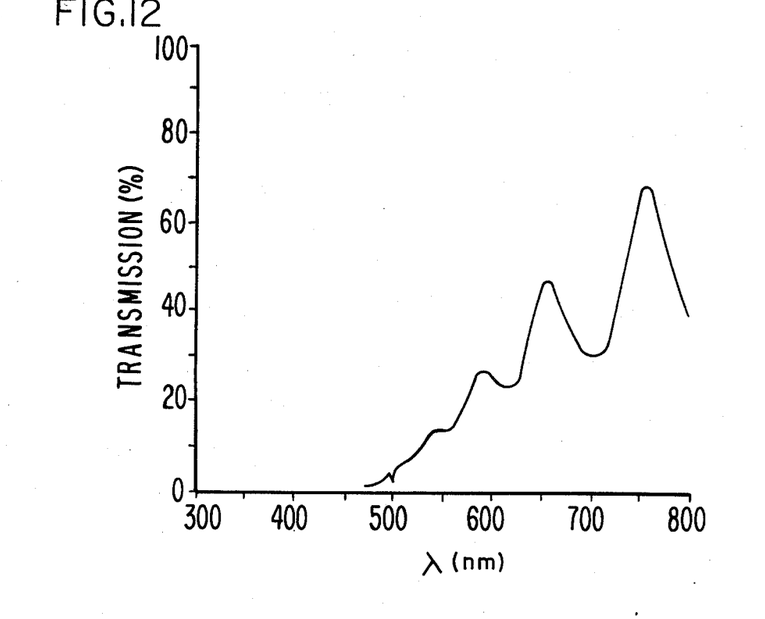
FIG. 12 is the measured transmission spectrum of a POQ water implanted with 100-keV As$^+$ at $1 \times 10^{12}$ cm$^{-2}$.

The transmission spectra of three implanted polysilicon-on-quarts wafers are presented in FIGS. 10–12. The wafers were implanted with 100-keV AS+ions at dose of $5 \times 10^{10}$ cm$^{-2}$, $1 \times 10^{11}$ cm$^{-2}$, and $1 \times 10^{12}$ cm$^{-2}$. Qualitative changes to the spectra that occur as the dose increases are the same as those mentioned earlier for silicon-on-sapphire wafers. Table IV summarizes the wavelengths at which the j=6 and j=7 maxima occur as a function of dose. The sensitivity to low-dose changes is about the same as it is for silicon-on-sapphire wafers. Thus, it will also be necessary to make transmission measurements on polysilicon-on-quartz wafers in the infrared in order to resolve dose changes of $1 \times 10^{10}$ cm$^{-2}$, i.e., to measure $1 \times 10^{12}$ cm$^{-2}$ dose implant uniformity to ±1%.

TABLE IV $\lambda_j$ versus dose for polysilicon-on-quartz wafer.

| Dose (cm$^{-2}$) | $\lambda_6$ (nm) | $\lambda_7$ (nm) |
|---|---|---|
| 0 | 749 | 649 |
| $5 \times 10^{10}$ | 751 | 652 |
| $1 \times 10^{11}$ | 754 | 654 |
| $1 \times 10^{12}$ | 758 | 658 |

Figure 13:
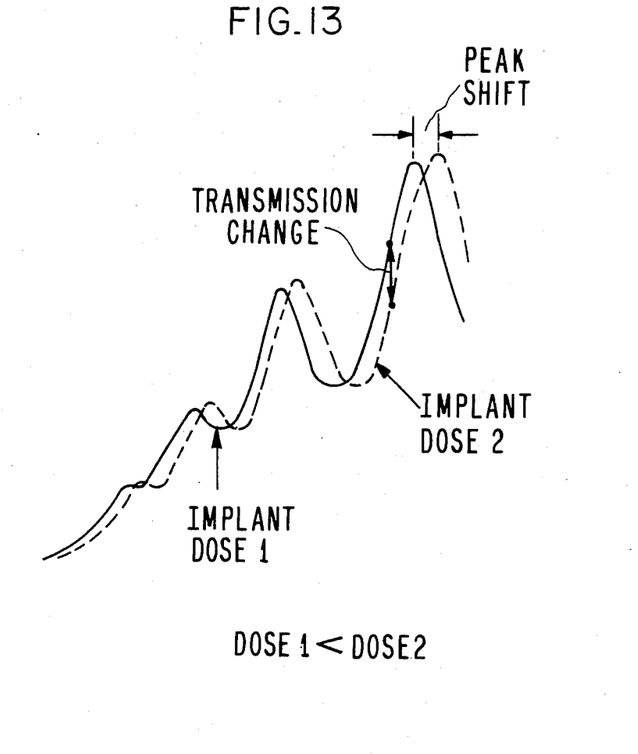
FIG. 13 is a schematic illustration showing how the transmission curve shifts with increasing implant dose.

Measurement of the transmission spectra of implanted silicon-on-sapphire and polysilicon-on-quartz wafers appears to be a promising implant dosimetry technique. By moving the wafer laterally with respect to the incident light (e.g., with an x-y stepping motor stage), maps of implant uniformity should be possible. The shift of the T($\lambda$) vs. $\lambda$ curve to higher $\lambda$ with increasing implant dose can be measured by the shift in peak position, as shown in Table II. This is best done in the infrared where peak shifts are the greatest. However, as a result of this shift, the transmission at a given wavelength also changes. These changes are most pronounced on the steep parts of the spectra (see illustration in FIG. 13). So, this measurement, which is easier to perform when mapping wafers, is best done at visible wavelengths where the derivative dT/d$\lambda$ is the greatest.

The method of the invention then comprises depositing a film of silicon or polysilicon thicker than the depth of the implant to be mapped on a sapphire, quartz, or oxidized silicon wafer. The film coating must be uniform in thickness and have a different index of refraction than the substrate. The substrate must be substantially transparent to the wavelength subsequently used to measure optical transmission. Examples would be silicon-on-sapphire or polysilicon-on-quartz. First, each wafer, whether used for calibration or dose measurement, is checked for uniformity of coating before ion implantation with a film thickness monitor such as an ellipsometer or by measuring the transmission coefficient at a few points. If the coating is not uniform, either the wafer is discarded or the pre-implant transmission data is recorded so that it can be substrated from the transmission map of the implanted wafer later. The wafer is then inserted in the ion implanter and a patter of implantation is generated. Test patterns could include uniform bands of implanted ions across the wafer from edge-to-edge which would test uniformity from center-to-edge and oscillatory non-uniformaties caused by lock-up of the control electronics. The test wafer is then removed from the implanter and loaded into a transmission spectrophotometer operating at a narrow wavelength band for measurement of implanted dose. The detector of the spectrophotometer measures the amount of light transmitted through the wafer at many points around the wafer (typically about 100) and the amount of light without the wafer. The ratio of the two quantities is the transmission coefficient for a given point on the wafer. The transmission coefficient is then converted to an implant dose by using previously-measured calibration curves for the ion energy and species implanted into the wafer under consideration.

Calibration curves are independently set up by measuring the transmission at the selected wavelength of several wafers implanted with known doses of a given ion. There is a different calibration curve for each ion species, implant energy, wafer thickness or selected wavelength.

The key to taking full advantage of the method according to the invention is choosing the appropriate wavelength of light at which transmission is measured. The wavelength must be one of those at which the rate of change of the transmissivity curve as a function of wavelength is a maximum. To a good approximation this may be taken as halfway between a maximum and a minimum in the transmission. The wavelength should also be chosen such that the transmission stays between the given maximum and the given minimum as the transmissivity shifts for the implant dose of interest. The bandwidth of the monochromator used must be sufficiently narrow to see the interference fringes, e.g. typically 0.5 nm but no more than 1 nm.

Figure 14:
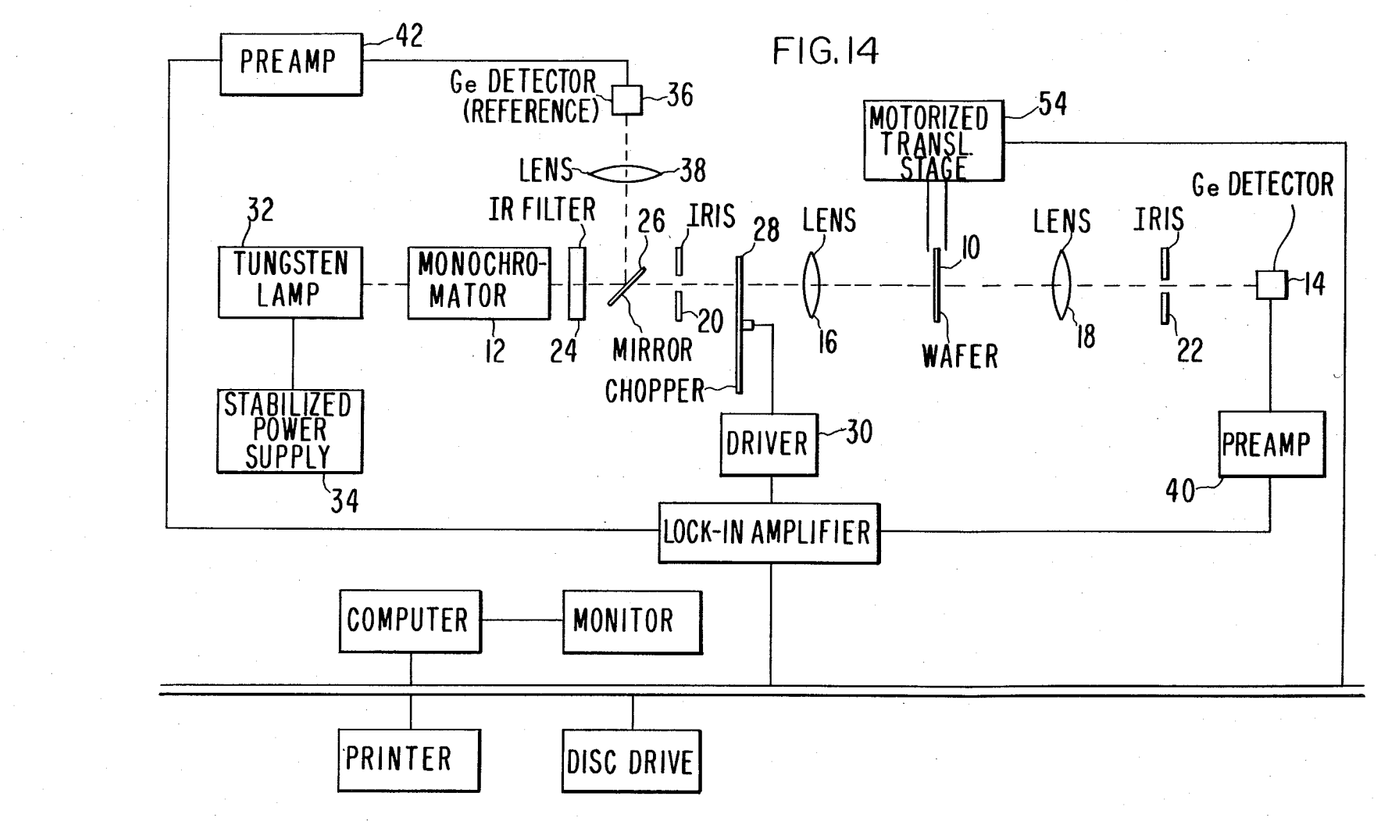
FIG. 14 is a block diagram of the apparatus used in the method of the invention.

Referring now to the drawings wherein reference numerals are used to designate parts throughout the various figures thereof, there is shown in FIG. 14, a block diagram of the apparatus used in the method of the invention. A wafer 10 on which has been generated a implanted ion test pattern is placed in the light path of a transmission spectrophotometer between the monochromator 12 and primary detector 14. Lenses 16, 18, irises 20, 22 and IR filter 24 and a partially-transmitting mirror 26 are also in the light beam to perform conventional functions of forming and splitting of the light beam. A light chopper 28 driven by a driver 30 is used to convert the DC signal from the primary detector 14 to an AC signal. The monochromator 12 is illuminated with a tungsten lamp 32 powered from a stabilized power supply 34. A reference beam of light from the mirror 26 is focussed on a reference detector 36 with a lens 38. The signals from the primary detector 14 and the reference detector 36 are passed through preamplifiers 40 and 42, respectively, to a lock-in amplifier 44. The lock-in amplifier 44 also receives the signal from the driver 30. The signal output from the lock-in amplifier is sent to a computer 46, having monitor 48, disc drive 50 and printer 52. The computer is used to control the motorized translation stage 54 on which the wafer 10 is mounted. The computer is also used to perform the calculation for the conversion of measured transmission coefficient to implanted dose, according to the invention.

The improved sensitivity of the method according to the invention comes from taking advantage of the interference phenomenon, which causes very rapid changes in the transmission spectrum as the wavelength or index of refraction is varied. None of the previous optical dosimetry work recognized or used this advantage. The index of refraction of photoresist, used in the prior art, is 1.6 while that of quartz is 1.46, so that reflectivity (see Eqn. 2) of the photoresist-on-quartz system is very small and the magnitude of the resulting interference oscillations is also quite small ($2 \cdot r_1 \cdot r_2 \cdot \exp[-\alpha d]$ from Eqn. 3), less than 1/10 of that of the method according to the invention. Also, the earlier silicon-on-sapphire work used a broad band of light wavelengths, thereby blurring the interference fringes together.

The sensitivity of the method of the invention can be seen from the transmission of polysilicon-on-quartz at a film thickness of 550 nm at an appropriate wavelength, i.e. $\lambda = 730$ nm. Table V gives the transmission for three different doses, as taken from FIGS. 10–12. Current instrumentation can resolve transmission changes of 0.01%, and so relative dose changes of 1% over the range $1 \times 10^{11}$ to $1 \times 10^{12}/$ cm$^2$ can be measured.

TABLE V

| Transmission at $\lambda = 730$ nm. | |
|---|---|
| Dose (As$^+$/cm$^2$) | Transmission (%) |
| $5 \times 10^{10}$ | 53 |
| $1 \times 10^{11}$ | 51 |
| $1 \times 10^{12}$ | 43 |

The method according to the invention also possesses several other versatile advantages. For example, the operating frequency can be chosen so that the transmission actually increases as the dose increases. Also, the sensitivity could be further increased by using an optical multichannel analyzer to record the entire spectrum and then calculating the derivative of the curve at a selected wavelength where the second derivative is a maximum (near a maximum or minimum of transmission). Finally, working in a reflection mode would give the same interference fringes, and thus good sensitivity, but would also allow oxidized silicon substrates to be used. Oxidized silicon substrates are close to real device wafers in many characteristics and are acceptable to ion implanter users.

This invention is not limited to the preferred embodiment and alternatives heretofore described, to which variations and improvements may be made including mechanically and electrically equivalent modifications to component parts, without departing from the scope of protection of the present patent and true spirit of the invention, the characteristics of which are summarized in the following claims.

What is claimed is:

1. A method of mapping ion dose uniformity, comprising the steps:
   (a) scanning wafers having a thin film or polysilicon coated on a substrate made of optically transparent material while measuring the optical transmission spectrum, thereby calibrating wafers suitable for subsequent steps,
   (b) inserting in the ion implantation device to be mapped a wafer calibrated in step (a),
   (c) implanting an ion dose in said thin layer of polysilicon in a controlled pattern,
   (d) removing said wafer from said ion implantation device,
   (e) scanning the wafer while measuring the optical transmission spectrum of the implanted film using essentially monochromatic radiation and a detection bandwidth of not more than 1 nm, and
   (f) calculating the dose distribution from the data of the optical transmission spectrum data, film thickness calibration data and calibration data from known ion implant doses.

2. The method of claim 1 in which the substrate comprises quartz.

3. The method of claim 1 where step (e) is performed at a wavelength selected at a midpoint between a minimum and a maximum in the interference transmission spectrum of the wafer measured before ion implantation.

4. A method of mapping ion dose uniformity, comprising the steps:
   (a) scanning wafers having a thin film of polysilicon coated on a substrate while measuring the optical reflection spectrum, thereby calibrating wafers suitable for subsequent steps,
   (b) inserting in the ion implantation device to be mapped a wafer calibrated in step (a),
   (c) implanting an ion dose in said thin layer of polysilicon in a controlled pattern,
   (d) removing said wafer from said ion implantation device,
   (e) scanning the wafer while measuring the optical reflection spectrum of the implanted film using essentially monochromatic radiation and a detection bandwidth of not more than 1 nm, and
   (f) calculating dose distribution from the data of the optical reflection spectrum data, film thickness calibration data, and calibration data from known ion implant doses.

5. The method of claim 4 in which the substrate comprises a wafer of silicon coated with a thin layer of silicon dioxide.

6. The method of claim 4 wherein step (e) is performed at a wavelength selected at a midpoint between a minimum and a maximum in the interference reflection spectrum of the wafer measured before ion implantation.

* * * * *